United States Patent [19]

George et al.

[11] Patent Number: 4,808,594

[45] Date of Patent: Feb. 28, 1989

[54] IMIDOPYRIDINES USEFUL IN THERAPY

[75] Inventors: Pascal George, Vtry sur Seine; John Allen, Voisins le Bretonneux, both of France

[73] Assignee: Synthelabo, France

[21] Appl. No.: 116,217

[22] Filed: Nov. 3, 1987

[30] Foreign Application Priority Data

Nov. 7, 1986 [FR] France ................... 86 15533

[51] Int. Cl.$^4$ ............ A61K 31/435; C07D 471/04
[52] U.S. Cl. .................... 514/300; 546/121
[58] Field of Search ................ 546/121; 514/300

[56] References Cited

U.S. PATENT DOCUMENTS 4,382,938 5/1983 Kaplan et al. ................... 546/121

OTHER PUBLICATIONS

Georges et al., Chem. Abst., vol. 107, 59031 (1987).

Primary Examiner—Mary C. Lee
Assistant Examiner—Bernard I. Dentz
Attorney, Agent, or Firm—Wegner & Bretschneider

[57] ABSTRACT

An imidazopyridine of formula (I)

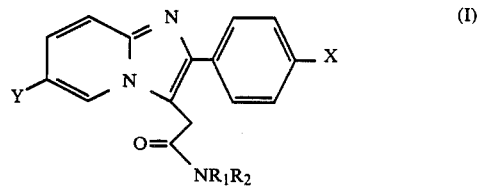

in which:
either X is $CH_3$ and Y is $CH_2$ OR,
or, X is $CH_2OR$ and Y is $CH_3$,
R is a $C_{1-6}$ alkyl group,
$R_1$ is a $C_{1-3}$ alkyl group, and
$R_2$ is a $C_{1-3}$ alkyl group, has useful anxidytic and hypnotic properties.

4 Claims, No Drawings

IMIDOPYRIDINES USEFUL IN THERAPY

The present invention relates to imidazopyridines, their preparation and their application in therapy.

The present invention provides an imidazopyridine of formula (I)

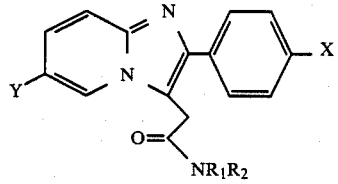
(I)

in which:
either X is $CH_3$ and Y is $CH_2OR$,
or X is $CH_2OR$ and Y is $CH_3$,
R is a $C_{1-6}$ alkyl group,
$R_1$ is a $C_{1-3}$ alkyl group, and
$R_2$ is a $C_{1-3}$ alkyl group.

The compound of formula (I) may be prepared according to the reaction schemes given in Appendices 1 and 2.

The present invention also provides a process for the preparation of a compound of formula (I) in which X is $CH_3$ and Y is $CH_2OR$ in which R is as defined above, in which a compound of formula (VI)

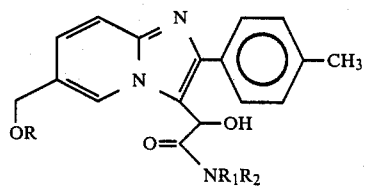
(VI)

in which R, $R_1$ and $R_2$ are as defined above is reacted with thionyl chloride and the compound obtained is reduced.

The compound of formula (VI) may be prepared by reducing an imidazo[1,2-a]pyridine of formula (III)

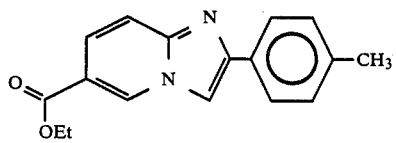
(III)

with lithium aluminium hydride to the corresponding alcohol of formula (IV)

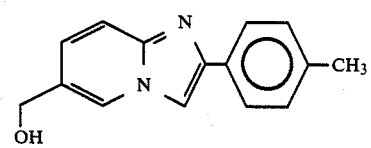
(IV)

which is then alkylated with an alkyl halide in the presence of a base to an ether of formula (V)

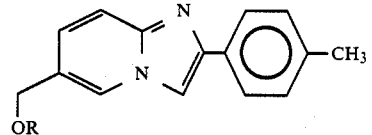
(V)

in which R is as defined above, and an acetamide chain is introduced by reacting the compound of formula (V) with N,N-dialkyl($R_1$, $R_2$)-glyoxylamide.

The present invention further provides a process for the preparation of a compound of formula (I) in which Y is $CH_3$ and X is $CH_2OR$ in which R is as defined above, in which a compound of formula (IX)

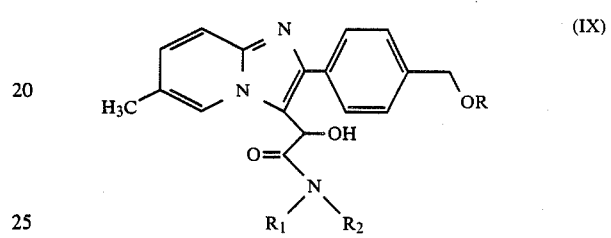
(IX)

is reacted with thionyl chloride and the compound obtained is reduced.

The compound of formula (IX) may be prepared by reducing an imidazo[1,2-a]pyridine of formula (II)

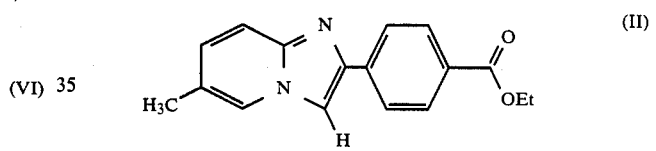
(II)

with lithium aluminium hydride to the corresponding alcohol of formula

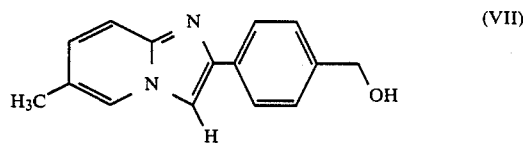
(VII)

which is then alkylated with an alkyl halide in the presence of a base to an ether of formula

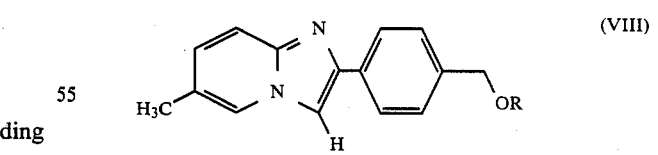
(VIII)

and an acetamide chain is introduced by reacting this compound with N,N-dialkyl($R_1$, $R_2$)-glyoxylamide.

The imidazo[1,2-a]pyridines of formulae (II) and (III) may be prepared according to the reaction schemes given in Appendix 3.

The compounds of formula (I) are active in the central nervous system region and possess anxiolytic, sleep-inducing, hypnotic and anticonvulsant properties; they are useful for treating anxiety states, sleep disorders and other neurological and psychiatric conditions.

The present invention also provides a pharmaceutical composition comprising an effective amount of a compound of formula (I) and a suitable excipient.

The composition may be in any form suitable for oral or parenteral administration, for example in the form of tablets, dragees, gelatin capsules, solutions to be taken by mouth or injectable solutions. Any suitable excipient may be used.

The daily dosage ranges, for example, from 0.5 to 2000 mg.

The present invention further provides a method of treating an anxiety state, sleep disorder or neurological or psychiatric condition which comprises administering to a subject suffering therefrom or liable to suffer therefrom an effective amount of a compound of formula (I).

The following Examples further illustrate the present invention. The analyses and the IR and NMR spectra confirm the structure of the compounds.

EXAMPLE 1

N,N-Dimethyl-2-(4-methylphenyl)-6-(methoxymethyl)imidazo[1,2-a]pyridine-3-acetamide (reaction scheme 1)

1. 6 g (17.7 mmol) of ethyl 2-(4-methylphenyl)imidazo[1,2-a]pyridine-6-carboxylate (III) (compound described in French Patent No. 85/06,918), 1 g (26.5 mmol) of lithium aluminium hydride and 180 ml of tetrahydrofuran are introduced into a round-bottomed flask maintained under argon. Stirring is maintained at 0° C. for 0.5 hour and the mixture is then hydrolyzed. The alcohol (IV) is extracted with $CH_2Cl_2$ and purified by column chromatography.

M.p. 183°–186° C.

2. 1.7 g (7.13 mmol) of compound (IV), 684 mg (14.26 mmol) of 50% strength NaH in oil and 2 g (14.26 mmol) of methyl iodide are introduced into a mixture of 35 ml of THF and 3.5 ml of DMF. The mixture is stirred in the cold for 40 mins, 5 ml of methanol are then added and the mixture is evaporated to dryness. The residue is taken up with water. The ether (V) is extracted with $CH_2Cl_2$. After drying, filtration and evaporation of the solvent, a beige solid is obtained, which is purified by column chromatography.

M.p. 113°–114° C.

3. The α-hydroxyacetamide (VI) is prepared in the following manner:

(a) 5.5 g (31.4 mmol) of N,N-dimethylglyoxylamide diethyl acetal and 0.286 g (0.77 ml; 7.84 mmol) of concentrated hydrochloric acid are reacted in 100 ml of acetic acid for 2 h at 50° C.

(b) 54 ml of the solution prepared above are treated with 1.27 g (15.45 mmol) of sodium acetate for ¼ h at 50° C., the imidazopyridine (V) is then added and the mixture is left at this temperature for 2 h. The mixture is evaporated to dryness and the residue taken up with water and dilute ammonia solution, and then $CH_2Cl_2$. The organic phase is decanted and dried and the solvent evaporated off: the residue is purified by chromatography on a silica column by means of a 97.5:2.5 $CH_2Cl_2$/methanol mixture.

The α-hydroxyacetamide (VI) melts at 188°–190° C.

4. The conversion of the compound (VI) to the compound (I) is carried out in two stages:

(a) 0.9 g (2.54 mmol) of α-hydroxyacetamide (VI) is dissolved in 50 ml of $CH_2Cl_2$, 5 ml of $SOCl_2$ are added dropwise and the mixture is left stirred for 20 h at room temperature. The solvent is evaporated off, the residue taken up with ether, then filtered and dried.

(b) 0.96 g (2.37 mmol) of the product obtained in 4. (a) is dissolved in 70 ml of $CH_2Cl_2$, 1.1 g of Rongalite is added and the mixture is left stirred at room temperature for 3 h. The insoluble material is filtered off and the filtrate washed with bicarbonate water and then with water to neutral pH. The organic phase is dried and the solvent then evaporated off. The evaporation residue is purified by chromatography on a silica column with a 98:2 $CH_2Cl_2$/methanol mixture.

The compound (I), N,N-dimethyl-2-(4-methylphenyl)-6-(methoxymethyl)imidazo[1,2-a]pyridine-3-acetamide, melts at 105°–106° C.

EXAMPLE 2

N,N,6-Trimethyl-2-[4-(methoxymethyl)phenyl]imidazo[1,2-a]pyridine-3-acetamide (reaction scheme 2)

1. 1.07 g ($2.8 \times 10^{-2}$ mol, 1.5 eq) of $LiAlH_4$ is added under an argon atmosphere to 5.3 g ($1.9 \times 10^{-2}$ mol) of ethyl 4-(6-methylimidazo[1,2-a]pyrid-2-yl)benzoate (II) [prepared from ethyl 4-(2-bromoacetyl)benzoate and 5-methyl-2-pyridinamine (see Appendix 3)] suspended in 190 ml of dry tetrahydrofuran (THF) and cooled in an ice bath. The mixture is left stirred for ¾ h at this temperature, then hydrolyzed and filtered on celite, the precipitate is washed several times with a 1:1 $CH_2Cl_2$/MeOH mixture and the extract then evaporated to dryness. This residue is purified by chromatography and crystallized in ether.

Yield=57%, m.p. 238°–239° C.

2. 1 g (2.07 mol, 2 eq) of 50% strength sodium hydride in oil and then 1.3 ml (2.07 mol, 2 eq) of iodomethane are added under an argon atmosphere to a suspension of 2.47 g ($1.03 \times 10^{-2}$ mol) of 6-methyl-2-[4-(hydroxymethyl)phenyl]imidazo[1,2-a]pyridine (VII) in a mixture of 50 ml of THF and 5 ml of dimethylformamide. The mixture is left stirred for 15 h at room temperature, the excess hydride is then hydrolyzed with 10 ml of methanol, the mixture is evaporated to dryness, the residue taken up between water and methylene chloride and the extract washed, dried and evaporated. The residue is purified by chromatography, crystallized in ether, filtered off and then dried.

Yield=85%, m.p. 158°–160° C.

3. 0.58 ml (0.25 eq) of concentrated HCl is added dropwise to 4.4 g ($2.4 \times 10^{-2}$ mol) of 2,2-(diethoxy)-dimethylacetamide dissolved in 90 ml of acetic acid, and in a bath at 50° C., and the mixture is left stirred for 2 h at this temperature. 2 g ($2.4 \times 10^{-2}$ mol) of sodium acetate are then added, the mixture is left for ¼ h and finally 2.2 g ($8.7 \times 10^{-3}$ mol) of 6-methyl-2-[4-(methoxymethyl)phenyl]imidazo[1,2-a]pyridine (VIII) are added; the heating is continued for 2 h and the mixture is then evaporated to dryness, the residue is taken up between $CH_2Cl_2$ and $H_2O$, and the organic phase is washed with dilute ammonia solution and then with water to neutral pH, dried and evaporated. The residual oil is purified by chromatography, crystallized in ether and dried.

Yield=52%, m.p. 152.5°–153.5° C.

4. 8.5 ml of thionyl chloride are added dropwise to 1.5 g ($4.2 \times 10^{-3}$ mol) of α-hydroxy-N,N-dimethyl-6-methyl-2-[4-(methoxymethyl)phenyl]imidazo[1,2-a]pyridine-3-acetamide (IX) dissolved in 85 ml of dry methylene chloride. The mixture is left stirred for 15 h at room temperature and evaporated to dryness, the residue is taken up with pentane, crystallized and dried under vacuum. A white solid is obtained which is dissolved in 120 ml of methylene chloride, 1.9 g ($1.2 \times 10^{-2}$ mol, 3 eq) of Rongalite are added and the mixture is left stirred for 4 h at room temperature. The mixture is then filtered and the filtrate washed with bicarbonate water and then with water to neutral pH, dried and evaporated. The product is purified by chromatography and crystallized in ether.

Yield=75%, m.p. 148°–149° C.

The compounds of the invention were subjected to the following pharmacological tests.

The sedative or hypnotic activity was determined by observing the action of the compounds on the ECoG of curarized rats [Depoortere H., Rev. E.E.G. Neurophysiol., (1980) 10, 3, 207–214]. In curarized rats, the test products are injected intraperitoneally or orally at increasing doses from 1 to 30 mg/kg. They induce sleep traces at doses equal to or greater than 0.3 mg/kg i.p.

The anticonvulsant activity of the compounds was determined according to the test of inhibition of pentetrazole-induced clonic convulsions in mice according to the method of Worms et al. (J. Pharmacol. Exp. Ther., 220: 660–671). In Charles River CD1 male mice (20–22 g), clonic convulsions are induced by the i.v. injection of 35 mg/kg of pentetrazole 30 min after the i.p. injection of the test product.

The $AD_{50}$ is the dose which protects 50% of the animals against the pentetrazole-induced clonic convulsions. The $AD_{50}$ of the compounds of the invention ranges from 0.1 to 10 mg/kg.

APPENDIX 1

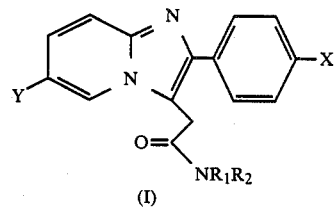

(I)

Scheme 1

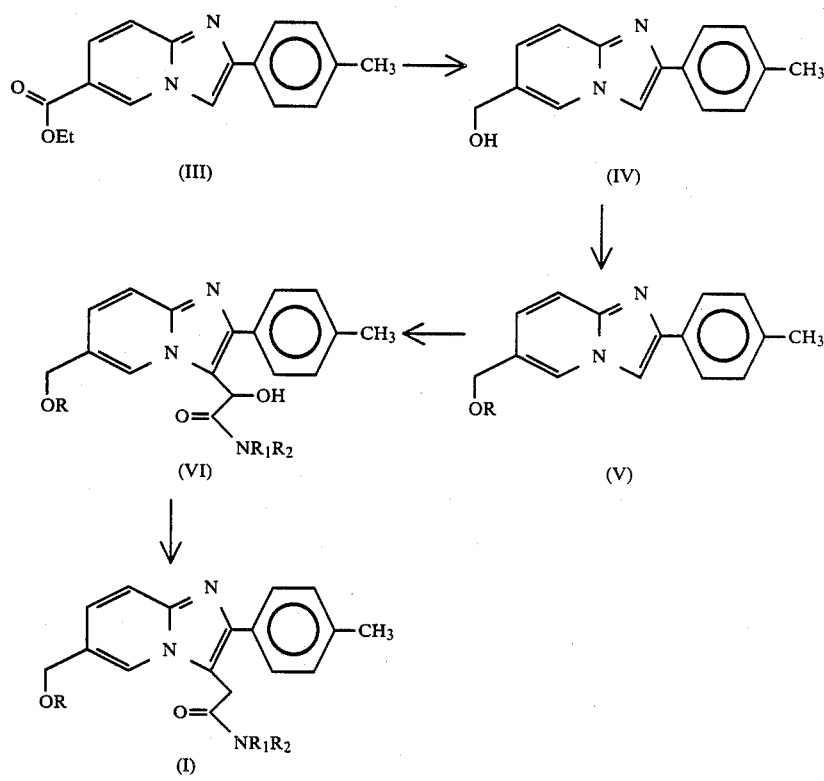

APPENDIX 2

Scheme 2

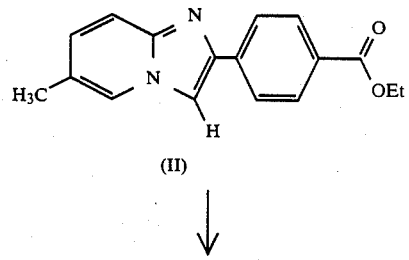

(II)

7

-continued
Scheme 2

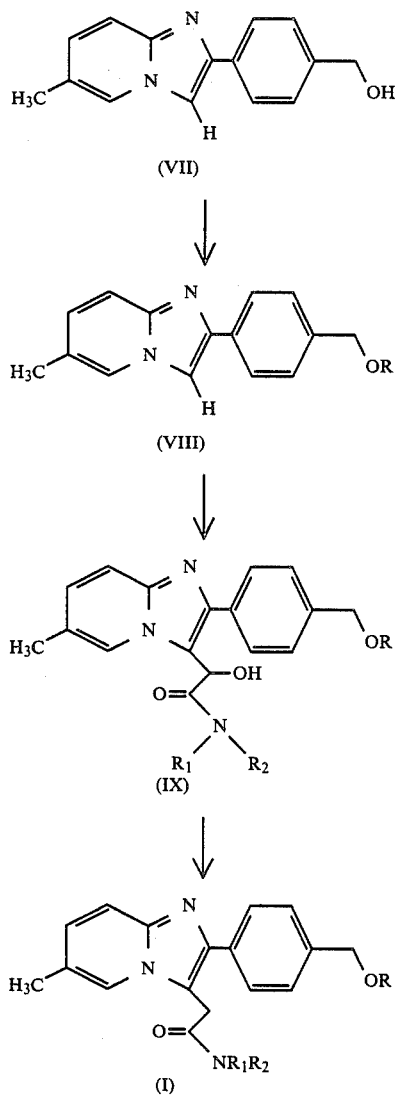

APPENDIX 3

Scheme 3

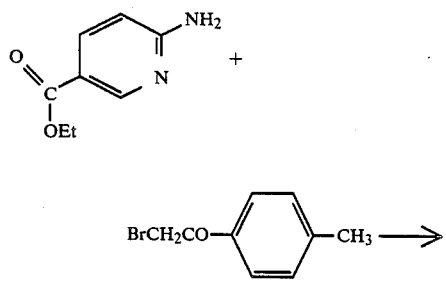

8

-continued
Scheme 3

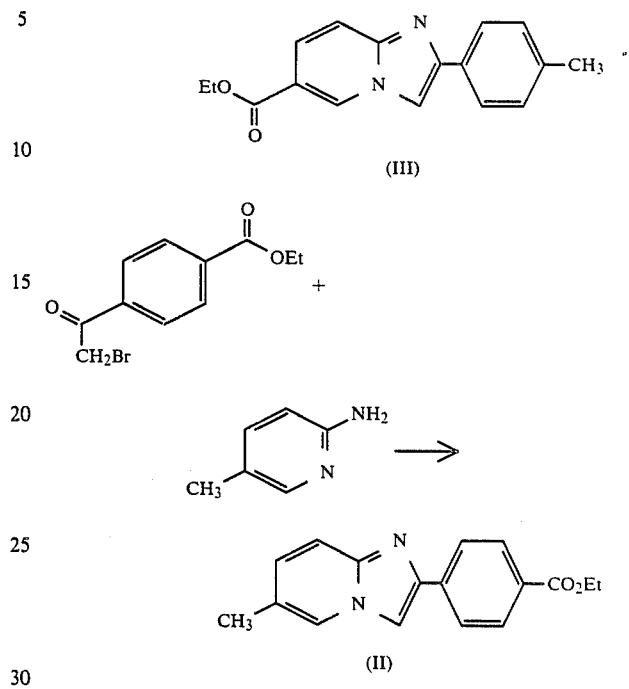

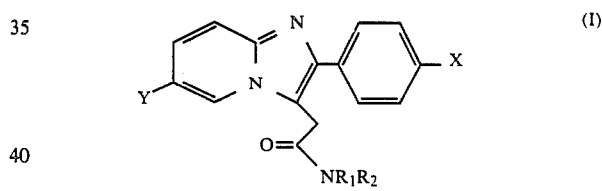

We claim:
1. An imidazopyridine of formula (I)

$$\text{(I)}$$

in which:
either X is $CH_3$ and Y is $CH_2OR$,
or X is $CH_2OR$ and Y is $CH_3$,
R is a $C_{1-6}$ alkyl group,
$R_1$ is a $C_{1-3}$ alkyl group, and
$R_2$ is a $C_{1-3}$ alkyl group.

2. An imidazopyridine according to claim 1 which is selected from the group consisting of N,N-dimethyl-2-(4-methylphenyl)-6-(methoxymethyl)-imidazo[1,2-a]pyridine-3-acetamide and N,N,6-trimethyl-2-[4-(methoxymethyl)phenyl]imidazo[1,2-a]pyridine-3-acetamide.

3. A method of treating an anxiety state, sleep disorder or neurological or psychiatric condition which comprises administering to a subject suffering therefrom or liable to suffer therefrom an effective amount of a compound as defined in claim 1.

4. A pharmaceutical composition for treatment of anxiety states and sleep disorders which comprises an effective anxiolytic or hypnotic amount of a compound of claim 1 and a pharmaceutically suitable excipient.

* * * * *